United States Patent

Seki et al.

[11] Patent Number: 5,585,403
[45] Date of Patent: Dec. 17, 1996

[54] STERILIZING AGENT FOR PREVENTING COCCIDIOSIS IN ANIMALS

[75] Inventors: Reiji Seki, Yono; Ryoji Kamimura, Tokyo; Satoru Mitsubayashi, Toda, all of Japan

[73] Assignee: Tamura Seiyaku Kabushiki Kaisha, Sakashita, Japan

[21] Appl. No.: 597,002

[22] Filed: Feb. 5, 1995

Related U.S. Application Data

[63] Continuation-in-part of Ser. No. 351,842, Dec. 7, 1994, abandoned.

[51] Int. Cl.$^6$ .......................... A01N 31/08; A01N 33/12; A01N 31/05; A01N 31/14
[52] U.S. Cl. .......................... 524/642; 514/736; 514/737; 514/751
[58] Field of Search .................................. 514/642, 751, 514/736, 737

[56] References Cited

U.S. PATENT DOCUMENTS

| | | | |
|---|---|---|---|
| 2,666,010 | 1/1954 | Stayner | 167/30 |
| 3,836,669 | 9/1974 | Dadekian | 424/329 |
| 4,434,166 | 2/1984 | Tanaka et al. | 424/250 |

*Primary Examiner*—Allen J. Robinson
*Attorney, Agent, or Firm*—Louise A. Foutch; Joseph C. Mason, Jr.

[57] ABSTRACT

A sterilizing agent comprising:

(A) a dichlorobenzene; and (B) a dialkyldimethylammonium halide represented by the formula

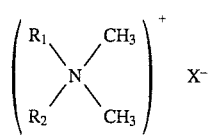

wherein X is bromine or chlorine, and, $R_1$ and $R_2$ each independently represent an alkyl group.

23 Claims, No Drawings

STERILIZING AGENT FOR PREVENTING COCCIDIOSIS IN ANIMALS

This application is a continuation-in-part of Ser. No. 08/351,842, filed Dec. 7, 1994, now abandoned.

BACKGROUND OF THE INVENTION

1. Field of the Invention

The present invention relates to a disinfectant or sterilizing agent for preventing coccidiosis in animals.

2. Description of the Related Art

Coccidium is a internal parasitic protozoan belonging to the genus of Eimeria and has been shown to infect a high percentage of poultry and rabbits and has thus has caused considerable damage to the poultry and farming industries. In addition, due to the recent pet boom, parasitism in dogs and cats has drastically increased. Countermeasures are urgently sought for the poultry and farming industries as well as the pet industry.

The damage caused by coccidium infections has been especially serious in the poultry industry. For example, avian fecal coccidiosis produces acute symptoms in chicks including hemorrhagic diarrhea, resulting in death within several days. Arian coccidiosis infestation of the small intestine of mature poultry produces chronic symptoms, however it rarely results in the death of mature poultry. Nevertheless, infections in mature poultry cause as much damage as fecal coccidiosis in chicks, because parasitic infection of the small intestine of mature poultry for long periods of time results in malnutrition. Countermeasures against coccidiosis are basically divided into two categories: (1) preventive measures to exterminate or decrease the source of infection, i.e. measures to irradicate coccidium oocysts, or to prevent or inhibit oocyst sporulation; and (2) therapeutic measures to hinder the metamorphosis of oocysts, and ultimately killing the oocysts in the intestinal tract of an infected animal.

As a general rule, the first category of countermeasures, treating the source of infection, is more important; in other words, it is more important to exterminate or decrease the source of infection, i.e. irradicate coccidium oocysts, or to prevent or inhibit oocyst sporulation into infectious mature oocyst, than to just treat infected animals. Coccidium oocysts, which are discharged outside the body of a host organism, are enclosed in scleroprotein and lipid which renders them highly resistant to elevated temperatures and environmental conditions, consequently oocysts cause repeated reinfections. Furthermore, various sterilizing agents which are effective for killing bacteria and viruses are ineffective at normal temperatures for killing coccidium oocysts.

The biological structure of infectious pathogens belonging to the Phylum Protozoa differs in Subphylum. Coccidium belongs to the Subphylum Apicomplexa. For example, Protozoan organisms belonging to the Subphyla Sarcomastigophora or Ciliophora have a very simple structure, while coccidium oocysts of the Subphylum Apicomplexa have a surface structure which is comprised of scleroprotein and lipid, as previously described. Further, organisms of the Subphyla Sarcomastigophora or Ciliophora reach their infectious maturity inside the body of the host organism and are very sensitive to environmental conditions and chemical agents. Coccidium oocysts which are discharged outside the body of the host organism have infectious ability after maturity. Specifically, the pathogenesis of coccidium oocysts is different from other Protozoan pathogens. In particular, coccidium oocysts reach their infectious maturity when discharged outside the body of the host organism. In addition, coccidium oocysts are highly resistant to harsh environmental conditions, extreme temperatures and chemicals.

Orthodichloric sterilizing agents are especially effective at inhibiting the sporulation of coccidium oocysts and have been widely used. However, orthodichloric sterilizing agents are not satisfactory because they are only slightly stronger than other sterilizing agents and they have virtually no effect on mature oocysts, those that have completed sporulation, which are found in the environment. Furthermore, orthodichloric sterilizing agents are not effective against general pathogens, therefore in actual sterilization regimes orthodichloric disinfectants must be used in conjunction with other disinfectants, and are therefore used alternatively and repeatedly with other disinfectants, thus, complicating the sterilization process.

Therefore a need exists to develop a sterilizing agent which is effective against coccidium oocysts and other pathogens in a single application.

SUMMARY OF THE INVENTION

The present invention discloses a sterilizing agent which has unexpected superiority in destroying oocysts, as well as sterilization capabilities which are superior against other general pathogens when compared with conventional orthodichloric disinfectants. These superior results are obtained by adding a dialkyldimethylammonium halide such as dialkyldimethylammonium chloride and dialkyldimethylammonium bromide and, in certain cases, a chlorophenol compound, represented by the formula as described below, to conventional dichlorobenzenes such as o-dichlorobenzene, dichlorobenzene or p-dichlorobenzene.

As described above, one essential component of the sterilizing agent of the present invention is a dichlorobenzene, preferably, o-dichlorobenzene is used; although m-dichlorobenzene and p-dichlorobenzene are also useful in the present invention.

Another component of the inventive sterilizing agent is a dialkyldimethylammonium chloride or a dialkyldimethylammonium bromide of the formula

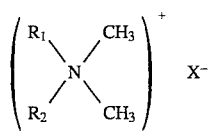

wherein X is bromine or chlorine, and $R_1$ and $R_2$ each independently represent an alkyl group having from 6 to 18 carbon atoms, and preferably having 10 carbon atoms. Examples of suitable combinations of $R_1$ and $R_2$ include the following:

| $R_1$ | $R_2$ |
|---|---|
| $C_8H_{17}$ | $C_8H_{17}$ |
| $C_8H_{17}$ | $C_{10}H_{21}$ |
| $C_{10}H_{21}$ | $C_{10}H_{21}$ |
| $C_{10}H_{25}$ | $C_{12}H_{25}$ |

One example of a preferred component for the inventive sterilizing agent is

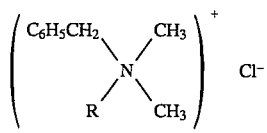

wherein R is an alkyl group having from 8 to 18 carbon atoms, and preferably having from 12 to 14 carbon atoms. A particularly suitable dialkyldimethylammonium chloride is didecyldimethylammonium chloride.

A further, but optional, component of the inventive agent is a chlorophenol compound of the formula

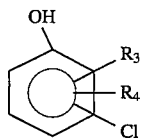

wherein $R_3$ and $R_4$, each independently represent hydrogen, a lower alkyl group having from 1 to 4 carbon atoms or phenyl, with the proviso that $R_3$ and $R_4$ may not both be hydrogen. Examples of suitable chlorophenol compounds include 4-chloro-2-methylphenol, 4-chloro-3-methylphenol, 2-chloro-4-methylphenol, p-chloro-o-amylphenol, p-chloro-n-amylphenol, p-chloro-o,n-amylphenol, p-chloro-o-hexylphenol, p-chloro-n-hexylphenol, p-chloro-o,n-hexylphenol, p-chloro-o-octylphenol, p-chloro-n-octylphenol, p-chloro-o,n-octylphenol, p-chloro-o-cyclopentylphenol, p-chloro-o-cyclohexylphenol, p-chloro-o-benzylphenol, 4-chloro-2,3-xylenol, 2-chloro-4,5-xylenol, 4-chloro-2,6-xylenol, 2-chloro-4,6-xylenol, 4-chloro-3,5-xylenol, 4-chloro-2,5-xylenol, 4-chloro-m-cresol, 4-chloro-o-phenylphenol and 2,4-dichloro-3,5-xylenol.

According to one embodiment of the invention, a compound, useful as a sterilizing agent for preventing coccidiosis, comprises a mixture of (a) o-dichlorobenzene, m-dichlorobenzene or p-dichlorobenzene; and, (b) dialkyldimethylammonium halide of the formula

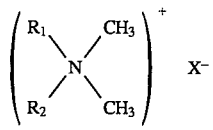

wherein X is bromine or chlorine, and $R_1$ and $R_2$, each independently represent an alkyl group having from 6 to 18 carbon atoms.

Another embodiment of the invention provides a compound, useful as a sterilization agent for preventing coccidiosis, comprising a mixture of (a) o-dichlorobenzene, m-dichlorobenzene or p-dichlorobenzene;

(b) dialkyldimethylammonium halide of the formula

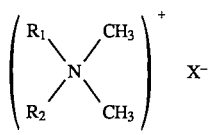

wherein X is bromine or chlorine, and $R_1$ and $R_2$ each independently represent an alkyl group having from 6 to 18 carbon atoms; and, (c) a chlorophenol compound of the formula

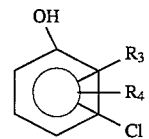

wherein $R_3$ and $R_4$, each independently represent hydrogen, a lower alkyl group having from 1 to 4 carbon atoms, or phenyl, with the proviso that $R_3$ and $R_4$ may not both be hydrogen.

A further embodiment of this invention provides a method for preventing coccidiosis in animals which comprises contacting the animal with an effective amount of a mixture of (a) o-dichlorobenzene, m-dichlorobenzene or p-dichlorobenzene; and, (b) a dialkyldimethylammonium halide of the formula

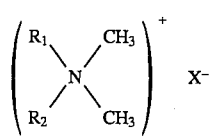

wherein X is bromine or chlorine, and $R_1$ and $R_2$ each independently represent an alkyl group having from 6 to 18 carbon atoms.

A still further embodiment of this invention provides a method for preventing coccidiosis in animals which comprises contacting the animals with an effective amount of a mixture of (a) o-dichlorobenzene, m-dichlorobenzene or p-dichlorobenzene;

(b) a dialkyldimethylammonium halide of the formula

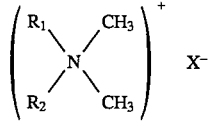

wherein X is bromine or chlorine, and $R_1$ and $R_2$ each independently represent an alkyl group having from 6 to 18 carbon atoms; and (c) a chlorophenol compound of the formula

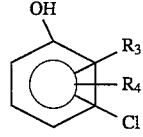

wherein $R_3$ and $R_4$, each independently represent hydrogen, a lower alkyl having from 1 to 4 carbon atoms, or phenyl, with the proviso that $R_3$ and $R_4$ may not both be hydrogen.

Other embodiments of this invention provide a method for enhancing the bactericidal activity of dichlorobenzenes used in treating coccidiosis comprising combining o-dichlorobenzene, m-dichlorobenzene or p-dichlorobenzene with a dialkyldimethylammonium halide of the formula

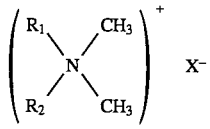

wherein X is bromine or chlorine, and $R_1$ and $R_2$ each independently represent an alkyl group having from 6 to 18 carbon atoms.

Other further embodiments of this invention provide methods of enhancing the bactericidal activity of dichlorobenzenes used for treating coccidiosis comprising combining o-dichlorobenzene, m-dichlorobenzene, or p-dichlorobenzene with a dialkyldimethyl-ammonium halide of the formula

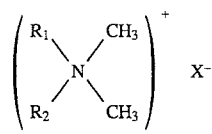

wherein X is bromine or chlorine, and $R_1$ and $R_2$ each independently represent an alkyl group having from 6 to 18 carbon atom; and a chlorophenol compound of the formula

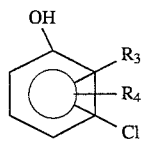

wherein $R_3$ and $R_4$, each independently represent hydrogen, a lower alkyl having from 1 to 4 carbon atoms, or phenyl, with the proviso that $R_3$ and $R_4$ may not both be hydrogen.

Although there can be considerable variation in the proportions of the dichlorobenzene, the didecyldimethyl-ammonium halide and the chlorophenol compound used in the inventive compositions, preferable percentages of dichlorobenzene, dialkyldimethylammonium halide and chlorophenol are in the range of 15 to 75 weight percent, 8 to 16 weight percent and 1 to 8 weight percent, respectively. Additional components, such as emulsifiers and other additives, may also be present in the inventive compositions. In a preferred embodiment o-dichlorobenzene is present in the inventive composition in the range of 55 to 75 weight percent, while p-dichlorobenzene and m-dichlorobenzene are effective in the inventive composition in an amount of from 15 to 30 weight percent.

The sterilizing agent of the present invention which is effective for preventing coccidiosis in animals contains the described compounds as essential components. These inventive compositions may be administered to animals and applied to the animal environment in various forms, though the most preferable form is as an emulsion. In order to make an emulsion, suitable surface-active agents, known in the art for obtaining a stable emulsified state may be added, as well as other additives known in the art which may be added should the necessity arise, such as, for example, cosolvents, copenetrants and stabilizers. The effective amount of the inventive sterilization agent which prevents coccidiosis can be determined by the degree of inhibition of the infestation involved. For example, it is effective to spread 1.0–1.5 l/m$^2$ of a 1:100 to a 1:400 dilution of an emulsion of the inventive composition over the floor or lower areas of the habitat for the infected animals, e.g. lower walls of a henhouse.

The above, and other objects, features and advantages of the present invention will become apparent from the following description.

DESCRIPTION OF PREFERRED EMBODIMENTS

1. Effect of the inventive compositions on avian coccidium oocysts.

Test Method

Chickens were infected with an NIAH (National Institute Animals Health) *Eimeria tenella* strain of acute fecal coccidium. Six days after infection unsporulated oocysts were harvested and separated from feces by a sucrose floatation method known in the art. A sample of unsporulated oocysts was diluted 1:400 and 6 mls of the dilution was added to 0.6 ml of an oocyst floating solution. The sample of unsporulated oocysts was then exposed to an emulsion of one of the inventive compositions at 25° C. for a period of 60 minutes. After treatment with the inventive composition, the unsporulated oocyst sample was washed during 4 cycles of centrifugal washing using a 0.5% aqueous solution of detergent prepared from a higher alcohol, with one cycle lasting 5 minutes at 2000 rpm. Then, the oocysts were floated in a 2% aqueous solution of potassium bichromate and incubated at 25° C. for a period of 5 days.

After the 5 day incubation period, 500 oocysts were examined under a microscope to observe the presence of sporulation. The degree of sporulation is shown as a percentage, with the sporulation rate of oocysts in the control solution (water in case of the present test) being 100%. The percent inhibition of sporulation of the inventive compounds is shown in Tables 1–3.

Test results for the inventive composition o-dichlorobenzene and didecyldimethylammonium chloride are shown in Table 1.

TABLE 1

Components of the inventive composition in weight percent
Dilution 1:400
Time 60 min.

| # | o-dichloro-benzene | didecyl dimethyl ammonium chloride | emulsifier and other additives | Sporulation Rate (%) | Inhibition of Sporulation (%) |
|---|---|---|---|---|---|
| 1 | 0 | 8.0 | 92.0 | 100 | 0 |
| 2 | 70.0 | 0 | 30.0 | 26.6 | 73.4 |
| 3 | 70.0 | 2.0 | 28.0 | 10.1 | 89.9 |
| 4 | 70.0 | 4.0 | 26.0 | 11.7 | 88.3 |
| 5 | 70.0 | 8.0 | 22.0 | 2.7 | 97.3 |
| 6 | 70.0 | 12.0 | 18.0 | 3.2 | 96.8 |

Test results for the inventive composition o-dichlorobenzene, didecyldimethylammonium chloride and 4-chloro-m-cresol are shown in Table 2.

TABLE 2

Components of the inventive composition in weight percent
Dilution 1:400
Time 60 min.

| | o-dichloro-benzene | didecyl dimethyl ammoniun chloride | 4-chloro-m-cresol | emulsifier and other additives | Sporulation Rate (%) | Inhibition of Sporulation (%) |
|---|---|---|---|---|---|---|
| 7 | 0 | 12.0 | 0 | 88.0 | 100 | 0 |
| 2 | 70.0 | 0 | 0 | 30.0 | 26.6 | 73.4 |
| 6 | 70.0 | 12.0 | 0 | 18.0 | 3.2 | 96.8 |
| 8 | 70.0 | 12.0 | 5.0 | 13.0 | 0.2 | 99.8 |

Test results for the inventive composition o-dichlorobenzene, didecyldimethylammonium chloride and 4-chloro-o-phenylphenol are shown in Table 3.

TABLE 3

Components of the inventive composition in weight percent
Dilution 1:400
Time 60 min.

| | o-dichloro-benzene | didecyl dimethyl ammoniun chloride | 4-chloro-o-phenol-phenol | emulsifier and other additives | Sporulation Rate (%) | Inhibition of Sporulation (%) |
|---|---|---|---|---|---|---|
| 7 | 0 | 12.0 | 0 | 88.0 | 100 | 0 |
| 2 | 70.0 | 0 | 0 | 30.0 | 26.6 | 73.4 |
| 6 | 70.0 | 12.0 | 0 | 18.0 | 3.2 | 96.8 |
| 9 | 70.0 | 12.0 | 5.0 | 13.0 | 1.4 | 98.6 |

Conventional orthodichloric disinfectants were tested in the same manner as explained above, the results of these tests are shown in Table 4.

TABLE 4

| Composition (active ingredients) | Sporulation Rate (%) | Inhibition of Sporulation (%) |
|---|---|---|
| o-dichlorobenzene (70.7 wt %) cresol chloride (7.3 wt %) | 81.1 | 18.9 |
| o-dichlorobenzene (75.0 wt %) 4-chloro-o-phenylphenol (5.0 wt %) xylenols (2.0 wt %) | 55.0 | 45.0 |
| o-dichlorobenzene (88.5 wt %) quinomethionate (1.5 wt %) | 1.9 | 98.1 |

2. Effect of the inventive compositions on general pathogens.

Test Method

The effectiveness of the inventive compositions against general pathogens was tested by means of measuring the phenol coefficient. Conventional orthodichloric compounds were similarly tested. All tests were conducted in accordance with the Sanitary Test Standard (Sterilizer Testing Standard) edited by the Ministry of Public Welfare using the bacteria *Salmonella typhi* H901W for the test.

Specifically, bacteria for the test were introduced into 10 mls of nutrient broth in a 15×180 mm test tube. The bacteria were successively cultivated at 37° C. The resultant subculture solution was used as the bacteria solution for the test. Various sterilizing agents were diluted with presterilized distilled water for the test. Diluted sample solutions of each sterilizing agent were divided into 25×170 mm test tubes under sterile conditions. Each test tube contained 10 ml diluted sterilizing agent, and was maintained at 20° C. in a thermostatic bath. Bacteria (1 ml) was introduced into the solution of each sterilizing agent, and the test tubes were thoroughly shaken in order to promote a reaction. Using a platinum loop made of platinum iridium (inner diameter: 4 mm; thickness: 0.6 mm; and length: 70 mm), one platinum loopful from each test tube was transplanted into an after-cultivation test tube containing nutrient broth and was incubated at a time of 2.5 minutes, 5 minutes, 10 minutes and 15 minutes after the reaction with sterilizing agent. After the transplantation, the culture media was cultivated in an incubator at 37° C. for 48 hours.

After cultivation, test tubes which had visible signs of bacterial growth were judged to be "+" and those which did not show the growth of bacteria were judged to be "−". The phenol coefficients referred to in the tables are the respective values of the maximum dilution strengths of the sterilizing agents, which produce a "+" result (the bacteria are not exterminated) after 5 minutes of sterilizing action and a "−" result (the bacteria are completely killed) after 10 minutes of sterilizing action, divided by the dilution strength of phenol which produces the same effect. Results of the tests are shown in Tables 5 and 6. All components are in weight percent.

TABLE 5

| | o-dichloro-benzene | didecyl dimethyl ammoniun chloride | 4-chloro-m-cresol | emulsifer and other additives | Phenol Coefficient |
|---|---|---|---|---|---|
| 10 | 0 | 10.0 | 0 | 90.0 | 210 |
| 5 | 70.0 | 8.0 | 0 | 22.0 | 170 |
| 8 | 70.0 | 12.0 | 5.0 | 13.0 | 210 |

TABLE 6

| Components | Phenol Coefficient |
| --- | --- |
| o-dichlorobenzene (75.0 wt %) 4-chloro-o-phenylphenol (5.0 wt %) xylenols (2.0 wt %) | 20 |
| o-dichlorobenzene (88.5 wt %) quinomethionate (1.5 wt %) | 50 |

As is evident in Table 1, the sterilizing agent containing o-dichlorobenzene, which has been widely used in the past, as its only disinfecting component (Sample No. 2), is ineffective for destroying oocysts or preventing their sporulation. Similarly, the disinfectant sample (Sample No. 1) containing didecyldimethylammonium chloride as its only disinfecting component was also ineffective for destroying oocysts or preventing their sporulation. On the other hand, it is evident that sterilizing agents according to the present invention, viz., sample Nos. 3–9, manifest very superior effects in destroying oocysts as well as restraining their sporulation.

Using the results shown in Table 1, the percent Inhibition Rate of Sporulation is calculated according to the following formula:

$$\frac{\text{Sporulation Rate of Control (water)} - \text{Sporulation Rate of Test Composition}}{\text{Sporulation Rate of Control}} \times 100.$$

For example, the percent inhibition rate of sporulation of the composition containing 8% by weight didecyldimethylammonium chloride:

$$\frac{100-100}{100} \times 100 = 0\% \text{ Inhibition Rate of Sporulation}$$

Coccidium oocysts treated with a composition containing 8% by weight didecyldimethylammonium chloride alone have a 0% inhibition rate of sporulation.

Using the same formula, coccidium oocysts treated with a composition containing 70% by weight of o-dichlorobenzene have an inhibition rate of sporulation of 73.4%. The expected additive effect on the inhibition rate of sporulation of didecyldimethyl ammonium chloride [inhibition=0%] and o-dichlorobenzene [inhibition=73.4%] would be an inhibition of sporulation of 73.4% [0%+73.4%]. However, the actual inhibition of sporulation as shown in Table 1, Sample 5 was 97.3% inhibition for the combination didecyldimethylammonium chloride and o-dichlorobenzene.

The difference between the expected additive effect (73.4%) and the actual effect of the combination didecyldimethylammonium chloride and o-dichlorobenzene, (97.3%) is a 32.6% greater inhibition in sporulation. This is calculated using the following formula:

$$\frac{\text{Actual Effect }(E) - \text{Expected Additive Effect }(EAE)}{\text{Expected Additive Effect }(EAE)} \times 100 = \% > EAE$$

Specifically:

$$\frac{[97.3\% - 73.4\%]}{73.4\%} \times 100 = 32.6\%$$

Clearly, these results are more than additive. Similar unexpected results were obtained for the other inventive compositions as shown in Tables 1–3. Specifically, as shown in Table 2, a disinfectant sample using 4-chloro-m-cresol added to a combination of o-dichlorobenzene and didecyldimethylammonium chloride also manifested a superior effect in destroying oocysts and restraining their sporulation. Similarly, the disinfectant sample using 4-chloro-o-phenylphenol added to a combination of o-dichlorobenzene and didecyldimethylammonium chloride also manifested superior effect in destroying oocyst and restraining sporulation.

In contrast as shown in Table 4, the examples of conventionally known sterilizing agents are considerably inferior to the inventive agents, as shown in Tables 1–3, concerning the killing of oocysts and restraining sporulation. Although, the conventionally known sterilizing agent combination, o-dichlorobenzene and quinomethionate, has nearly the same effect in destroying coccidium oocysts and restraining their sporulation as that of the inventive compositions it is functionally inferior. Specifically, as shown in Table 6, this conventional combination is considerably inferior to the compositions of the present invention concerning their general bactericidal effect as evidenced by an inadequate phenol coefficient. Accordingly, sterilizing agents according to the present invention not only have superior effects in destroying coccidium oocysts and restraining their sporulation but also are vastly superior to conventional disinfectants for simultaneously exhibiting superior bactericidal effect against other general pathogens.

Having described preferred embodiments of the invention it is to be understood that the invention is not limited to those precise embodiments, and that various changes and modifications may be effected therein by one skilled in the art without departing from the scope or spirit of the invention as defined in the appended claims.

We claim:

1. A disinfectant composition comprising synergistic effective amounts of:

from 15 to 75 percent by weight of a dichlorobenzene selected from the group consisting of o-dichlorobenzene, m-dichlorobenzene and p-dichlorobenzene; and from 8 to 16 percent by weight of a dialkyldimethylammonium halide of the formula

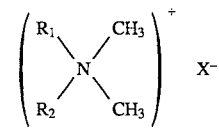

wherein,

X is selected from the group consisting of bromine and chlorine, and $R_1$ and $R_2$ each independently represent alkyl groups having from 6 to 18 carbon atoms.

2. A disinfectant composition comprising synergistic effective amounts of:

from 15 to 75 percent by weight of a dichlorobenzene selected from the group consisting of o-dichlorobenzene, m-dichlorobenzene and p-dichlorobenzene;

from 8 to 16 percent by weight of a dialkyldimethylammonium halide of the formula

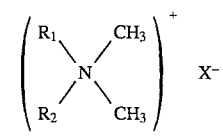

wherein,

X is selected from the group consisting of bromine and chlorine, and $R_1$ and $R_2$ each independently represent alkyl groups having from 6 to 18 carbon atoms; and from 1 to 8 percent by weight of a chlorophenol compound of the formula

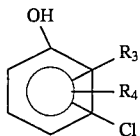

wherein, $R_3$ and $R_4$ each independently represent hydrogen, a lower alkyl group having from 1 to 4 carbon atoms, or phenyl, with the proviso that $R_3$ and $R_4$ are not both hydrogen.

3. The composition according to claim 1 wherein the dialkyldimethylammonium halide is dialkyldimethylammonium chloride.

4. The composition according to claim 1 wherein the dialkyldimethylammonium halide is didecyldimethylammonium chloride.

5. The composition according to claim 1 wherein the dichlorobenzene is o-dichlorobenzene.

6. The composition according to claim 2 wherein the dialkyldimethylammonium halide is dialkyldimethylammonium chloride.

7. The composition according to claim 2 wherein the dialkyldimethylammonium halide is didecyldimethylammonium chloride.

8. The composition according to claim 2 wherein the dichlorobenzene is o-dichlorobenzene.

9. The composition according to claim 2 wherein the chlorophenyl compound is 4-chloro-m-cresol.

10. The composition according to claim 2 wherein the chlorophenyl compound is 4-chloro-o-phenylphenol.

11. A disinfectant composition for preventing coccidiosis in animals comprising synergistic effective amounts of a mixture of from 15 to 75 percent by weight of o-dichlorobenzene and from 8 to 16 percent by weight of didecyldimethylammonium chloride.

12. A disinfectant composition for preventing coccidiosis in animals comprising synergistic effective amounts of a mixture of from 15 to 75 percent by weight of o-dichlorobenzene, from 8 to 16 percent by weight of didecyldimethylammonium chloride and from 1 to 8 percent by weight of 4-chloro-m-cresol.

13. A disinfectant composition for preventing coccidiosis in animals comprising synergistic effective amounts of a mixture of from 15 to 75 percent by weight of o-dichlorobenzene, from 8 to 16 percent by weight of didecyldimethylammonium chloride and from 1 to 8 percent by weight of 4-chloro-o-phenylphenol.

14. A method for preventing coccidiosis in animals comprising:

contacting an animal with a synergistic effective amount of a composition comprising from 15 to 75 percent by weight of a dichlorobenzene selected from the group consisting of o-dichlorobenzene, m-dichlorobenzene and p-dichlorobenzene; and from 8 to 16 percent by weight of a dialkyldimethylammonium halide of the formula

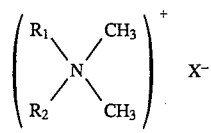

wherein

X is selected from the group consisting of bromine and chlorine, and $R_1$ and $R_2$ each independently represent alkyl groups having from 6 to 18 carbon atoms.

15. A method for preventing coccidiosis in animals comprising:

contacting an animal with a synergistic effective amount of a composition comprising from 15 to 75 percent by weight of a dichlorobenzene selected from the group consisting of o-dichlorobenzene, m-dichlorobenzene and p-dichlorobenzene;

from 8 to 16 percent by weight of a dialkyldimethylammonium halide of the formula;

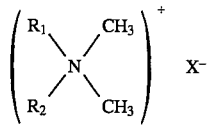

wherein,

X is selected from the group consisting of bromine and chlorine, and $R_1$ and $R_2$ each independently represent alkyl groups having from 6 to 18 carbon atoms; and from 1 to 8 percent by weight of a chlorophenol compound of the formula

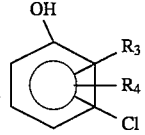

wherein, $R_3$ and $R_4$ each independently represent hydrogen, a lower alkyl group having from 1 to 4 carbon atoms, or phenyl, with the proviso that $R_3$ and $R_4$ are not both hydrogen.

16. The method according to claim 14 wherein the dichlorobenzene is o-dichlorobenzene and the dialkyldimethylammonium halide is didecyldimethylammonium chloride.

17. The method according to claim 15 wherein the dichlorobenzene is o-dichlorobenzene, the dialkyldimethylammonium halide is didecyldimethylammonium chloride and the chlorophenyl compound is 4-chloro-m-cresol.

18. The method according to claim 15 wherein the dichlorobenzene is o-dichlorobenzene, the dialkyldimethylammonium halide is didecyldimethylammonium chloride and the chlorophenyl compound is 4-chloro-o-phenylphenol.

19. A method for preventing coccidiosis in animals comprising:

spreading on an animal habitat a synergistic effective amount of a disinfectant composition comprising from 15 to 75 percent by weight of a dichlorobenzene selected from the group consisting of o-dichlorobenzene, m-dichlorobenzene and p-dichlorobenzene; and from 8 to 16 percent by weight of a dialkyldimethylammonium halide of the formula

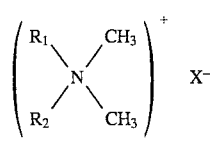

wherein,

X is selected from the group consisting of bromine and chlorine, and $R_1$ and $R_2$ each independently represent alkyl groups having from 6 to 18 carbon atoms.

20. A method for preventing coccidiosis in animals comprising:

spreading on an animal habitat a synergistic effective amount of a disinfectant composition comprising from 15 to 75 percent by weight of a dichlorobenzene selected from the group consisting of o-dichlorobenzene, m-dichlorobenzene and p-dichlorobenzene;

from 8 to 16 percent by weight of a dialkyldimethylammonium halide of the formula;

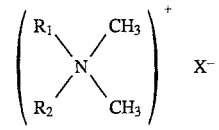

wherein

X is selected from the group consisting of bromine and chlorine, and $R_1$ and $R_2$ each independently represent alkyl groups having from 6 to 18 carbon atoms; and from 1 to 8 percent by weight of a chlorophenol compound of the formula

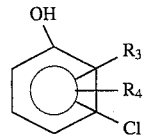

wherein, $R_3$ and $R_4$ each independently represent hydrogen, a lower alkyl group having from 1 to 4 carbon atoms, or phenyl, with the proviso that $R_3$ and $R_4$ are not both hydrogen.

21. The method according to claim 19 wherein the dichlorobenzene is o-dichlorobenzene and the dialkyldimethylammonium halide is didecyldimethylammonium chloride.

22. The method according to claim 20 wherein the dichlorobenzene is o-dichlorobenzene, the dialkyldimethylammonium halide is didecyldimethylammonium chloride and the chlorophenyl compound is 4-chloro-m-cresol.

23. The method according to claim 20 wherein the dichlorobenzene is o-dichlorobenzene, the dialkyldimethylammonium halide is didecyldimethylammonium chloride and the chlorophenyl compound is 4-chloro-o-phenylphenol.

* * * * *